United States Patent [19]

Schwartz

[11] Plant 4,265

[45] June 13, 1978

[54] ROSE PLANT

[75] Inventor: Ernest Schwartz, Kingsville, Md.

[73] Assignee: F. Harmon Saville, Rowley, Mass.

[21] Appl. No.: 821,783

[22] Filed: Aug. 4, 1977

[51] Int. Cl.[2] ..... A01H 5/00
[52] U.S. Cl. ..... Plt./8
[58] Field of Search ..... Plt./8

*Primary Examiner*—Robert E. Bagwill
*Assistant Examiner*—James R. Feyrer
*Attorney, Agent, or Firm*—Vincent G. Gioia

[57] ABSTRACT

A yellow miniature rose plant seedling, from "Gold Coin" × an unknown pollen parent, having a high, yellow blossom display, an absence of thorns and prickles, and high shade tolerance.

1 Drawing Figure

The present invention relates to a new and distinct variety of rose plant of the minature rose class, which was originated by my crossing as seed parent a seedling of the rose known as "Gold Coin" and an unknown seedling as pollen parent.

Among the novel characteristics possessed by this new variety which distinguish it from its parents and all other varieties of which I am aware are: (1) recurrent blooms of light yellow coloring, (2) high displaying high centered form singly and in sprays but with a form typical of hybrid tea plants, (3) plants which grow particularly well indoors under lights and outdoors in reduced-light conditions, and (4) plants which grow well on own roots due to strong tendency for root development. Asexual reproduction by budding of the new variety as performed in Essex County, Mass., shows that the foregoing and other distinguishing characteristics come true to form and are established and transmitted through succeeding propagations.

The new and improved rose variety which I have developed is an unusually fine miniature rose of light yellow coloring, bearing blooms of high centered, hybrid-tea like form both singly and in sprays. The usefulness of the plant is greatly enhanced by its ability to grow well under reduced-light, e.g. shade, conditions outdoors. However, one of its most valuable characteristics is its performance under lights which makes it a valuable greenhouse variety. The flowers last well on the plant and tend to lighten in color on aging. The plant itself is attractive in combining small, abundant foliage with well branching growth. Another especially desirable feature of this new variety is that it has virtually no thorns.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "6D" is plate 6D of the Royal Horticultural Society Color Chart.

Parentage:

*Seed parent.*—A seedling of "Gold Coin."

*Pollen parent.*—"Unknown Seedling."

Class: Miniature.

The following observations are made of specimens grown in a greenhouse at Essex County, Mass. during the month of May.

FLOWER

Blooming habit: Continuous.

Bud:

*Size.*—Medium.

*Form.*—Ovate-pointed.

*Color.*—When sepals first divide — 3B to 3C. When petals begin to unfurl — 8B to 8C. When half-blown: 6D. Reverse side of petals — 6D.

*Sepals.*—Extend beyond bud, feathered appearance.

*Peduncle.*—Length — about 1 inch. Aspect — straight. Strength — erect, adequate strength to support bloom. Color — Approx. 145A to 144A.

Bloom:

*Size.*—Average size when fully expanded — about 1 to 1½ inch.

*Borne.*—Singly and several together in open sprays.

*Form.*—High centered blooms, becoming flat upon opening, petals quilling at the top.

*Petalage.*—Number of petals under normal conditions — about 20 to 24.

*Color.*—(during first 2 days).—Inner petals at center of flower — 8B. Outer petals — 8C to 8D. Base of petals (point of attachment) — 6C. Reverse of petals — 6D. General tonality from a distance — 8C.

*Color change.*—As bloom ages — outer part of petals lighten to 8D and after several days to 11D.

Petals:

*Texture.*—Medium.

*Appearance.*—Satiny inside and outside.

*Form.*—Rounded, elongated toward point of attachment.

*Arrangement.*—Imbricated.

*Petaloids in center.*—Few.

*Persistence.*—Quite persistent for a time and then drop.

*Fragrance.*—Delicate — slight.

*Lasting quality.*—Color lightens and lasts long on plant.

REPRODUCTIVE ORGANS

Stamens, filaments and anthers:

*Arrangement.*—Regularly arranged around stiles.

*Color.*—17A, filaments — 10A.

Pollen: Color — 17B but only slight amount.

Styles: Even, medium length.

Stigmas: Color — 2D.

Hips: Almost none.

PLANT

Form: Compact, bushy.

Growth: Vigorous, uniform branching, attains height of 8 to 10 inches.

Foliage: Compound of three to five leaflets.

*Size.*—Small.

*Quantity.*—Abundant.

*Color.*—New foliage: Upper side — near to 189A. Under side — near to 138C. Old foliage: Upper side — 132A. Under side — 138C.

*Shape.*—Oval, pointed.

*Texture.*—Upper side — flat matt. Under side — marked veining.

*Edge.*—Serrated.

*Serration.*—Deeper and more pointed toward leaf tip.

*Leaf stem.*—Color — near to 138B. Under side — 138A.

*Stipules.*—Long ($\frac{3}{8}$-inch) with long points.

*Resistance to disease.*—Blackspot — good. Mildew — good.

Wood:

*New wood.*—Color — near 138C. Bark — smooth.

*Old wood.*—Color — 137C. Bark — slight roughness.

Thorns:

*Thorns.*—Quantity: none observed on main stalks from base and laterals.

*Prickles.*—None.

Winter hardiness: Good winter hardiness, needs protection only in extreme climate.

I claim:

1. A new and distinct variety of rose plant of the miniature class, substantially as shown and described, characterized particularly by high centered, recurrent flowers of light yellow coloring which are long lasting on the plant until dropping and grown on a vigorous plant with abundant foliage and virtually no thorns which can grow well in reduced light.

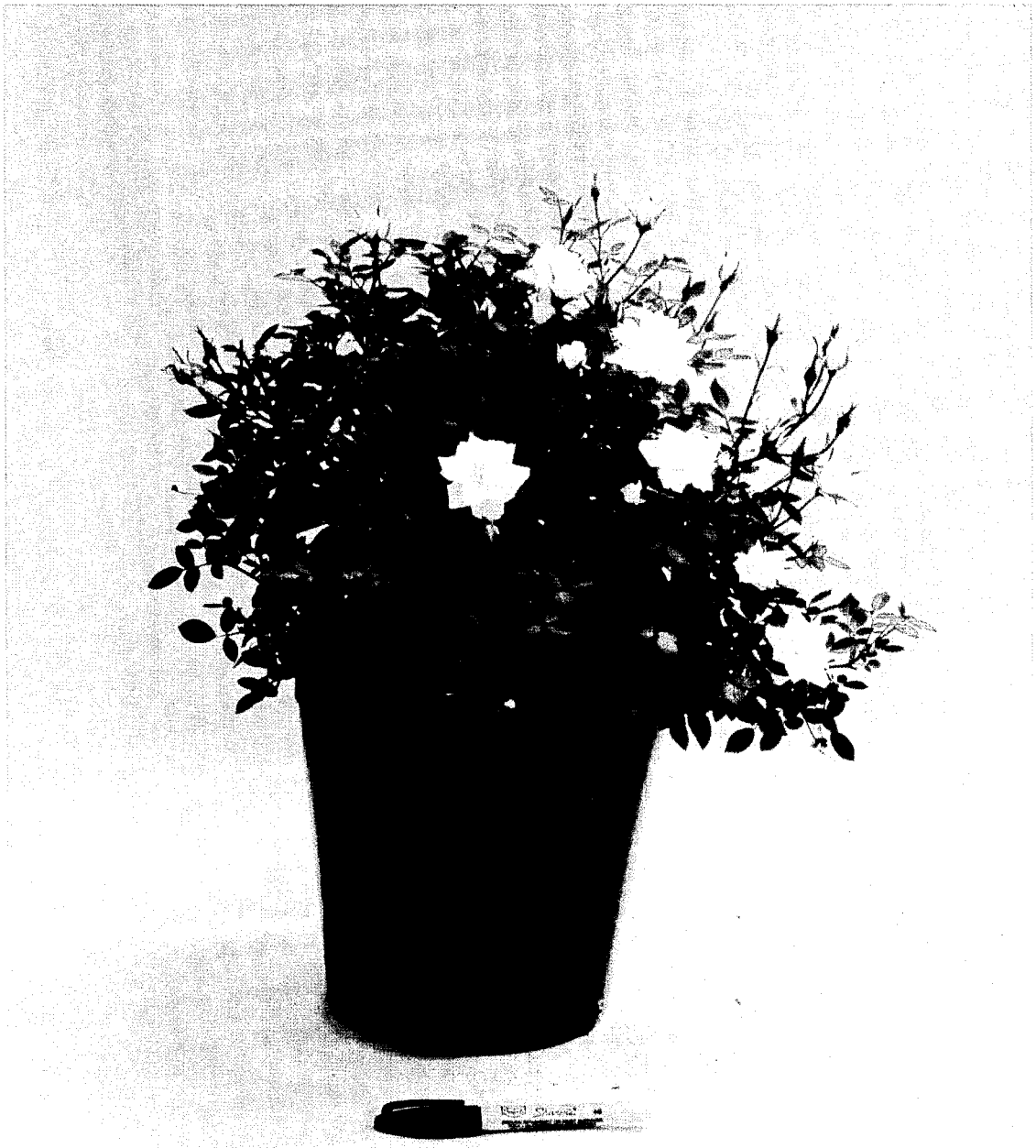

* * * * *